US00PP16386P3

(12) United States Plant Patent
Danziger

(10) Patent No.: US PP16,386 P3
(45) Date of Patent: Mar. 28, 2006

(54) ***PETUNIA* PLANT NAMED 'DANCASBIPAS'**

(50) Latin Name: *Petunia sensu*
Varietal Denomination: Dancasbipas

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 150 days.

(21) Appl. No.: 10/829,220

(22) Filed: Apr. 22, 2004

(65) Prior Publication Data

US 2005/0241041 P1 Oct. 27, 2005

(51) Int. Cl.
*A01H 5/00* (2006.01)

(52) U.S. Cl. ..... Plt./356

(58) Field of Classification Search ..... Plt./356
See application file for complete search history.

(56) References Cited

U.S. PATENT DOCUMENTS

PP11,971 P2 * 7/2001 Heffner ..... Plt./356
PP12,101 P2 * 9/2001 Sakazaki ..... Plt./356
PP14,125 P2 * 9/2003 Miyazaki ..... Plt./356

* cited by examiner

*Primary Examiner*—Kent Bell
*Assistant Examiner*—W. C. Haas
(74) *Attorney, Agent, or Firm*—Foley & Lardner, LLP

(57) ABSTRACT

A new and distinct *Petunia* plant named 'Dancasbipas' particularly characterized by its flower color: five white strips over pink background; very floriferous and very long blooming season; vigorous, cascading growth habit; good weather tolerance; and suitable for patios and outdoors bedding.

2 Drawing Sheets

Botanical designation: *Petunia sensu* Wijsman.
Variety denomination: 'Dancasbipas'.

BACKGROUND OF THE INVENTION

The present invention relates to a new and distinct cultivar of *Petunia* plant, botanically known as *Petunia sensu* Wijsman, hereinafter referred to by the cultivar name 'Dancasbipas'.

The new cultivar originated from cross made in a controlled breeding program in Moshav Mishmar Hashiva, Israel. The female parent is a proprietary cultivar designated CV-52 (unpatented). The male parent is a proprietary cultivar designated CV-144 (unpatented). 'Dancasbipas' was discovered and selected by the inventor, Gabriel Danziger, as a flowering plant within the progeny of the stated cross in a controlled environment in Moshav Mishmar Hashiva, Israel.

Asexual reproduction of the new cultivar by cutting of side shoots, was first performed in February, 2003 in Moshav Mishmar Hashiva, Israel, and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be basic characteristics of 'Dancasbipas' which in combination distinguish this *Petunia* as a new and distinct cultivar:

1. Flower color: five white stripes over pink background;
2. Very floriferous and very long blooming season;
3. Vigorous, cascading growth habit;

4. Good weather tolerance; and
5. Suitable for patios and outdoors bedding.

'Dancasbipas' has not been observed under all possible environmental conditions. The phenotype of the new cultivar may vary with variations in environment such as temperature, light intensity, and day length without any change in the genotype of the plant. The following observations, measurements and values describe the new cultivar as grown in Moshav Mishmar Hashiva, Israel under conditions, which closely approximate those generally used in commercial practice.

Plants of 'Dancasbipas' differ from plants of the parental cultivars, 'CV-52' and 'CV-144' in the following characteristics:

TABLE 1

| Character | 'Dancasbipas' | Female parent - 'CV-52' | Male parent - 'CV-144' |
|---|---|---|---|
| Flowering time: | Early, Spring | Late Summer | Mid Summer |
| Leaf size: | Medium | Medium | Small |
| Growth habit: | Vigorous, well branched, semi bush | Vigorous, well branched | Medium Vigor and not well branched |

Of the many commercial cultivars known to the present inventor, the most similar in comparison to 'Dancasbipas' is the cultivar 'Cascadias Bicolor Lavender' (unpatented).

TABLE 2

| Characteristic | 'Dancasbipas' | Cascadias Bicolor Lavender |
|---|---|---|
| Flowering time | Early; spring, 8 weeks from planting | Medium; summer, 10 weeks from planting |

TABLE 2-continued

| Characteristic | 'Dancasbipas' | Cascadias Bicolor Lavender |
|---|---|---|
| Leaf size | Medium, length: 7.5 cm width: 2.5 cm to 3 cm | Large, length: 12.5 cm width: 5 cm |
| Growth habit | Vigorous well branched, semi-bush, height about 25 cm | Medium, cascading, height - 15 cm to 20 cm |

BRIEF DESCRIPTION OF THE DRAWING

The accompanying photographic drawings illustrate the overall appearance of the new *Petunia* showing the colors as true as is reasonably possible with colored reproductions of this type. In the photographs, 'Dancasbipas' is labeled by the designation 6031.

The first photograph shows a top view of a flowering 'Dancasbipas' plant.

The second photograph shows a side view of a flowering plant of 'Dancasbipas' at 3 months.

DETAILED BOTANICAL DESCRIPTION

The following observations, measurements and values describe the new cultivar as grown in Moshav Mishmar Hashiva, Israel under conditions which closely approximate those generally used in commercial practice. 'Dancasbipas' is for use as a pot plant and a bedding plant. Grown outdoors in moderate climate, indoors during winter. Irrigation and fertilization are needed on a regular basis. For optimal growth, grow in full sunlight 'Dancasbipas' plants are fully grown in 3 months. 'Dancasbipas' blooms year-round in moderate climate. Color references are made to The Royal Horticultural Society Colour Chart (R.H.S.) 2001 edition, except where general colors of ordinary significance are used. Color values were taken under daylight conditions at approximately noon in Moshav Mishmar Hashiva, Israel. The age of the plant described is 3 months.

Plant:

General appearance and form:

*Height.*—25 cm.

*Spread.*—30 inches.

*Growth habit.*—Bush cascading.

*Growth rate.*—Fully grown in 3 months.

*Branching habit and description.*—Normal branching habit, typical to *Petunia* species.

*Flowering response.*—Long day facultative.

*Flowering season.*—Year round in moderate climate.

*Winter hardiness/weather tolerance.*—Frost tender, plants may be damaged in temperatures below 5° C.

*Lastingness of the individual bloom.*—2 to 4 days.

*Rooting habit.*—From cutting base.

*Time to initiate roots.*—1 week.

*Time to produce a rooted cutting.*—2 to 3 weeks.

*Fragrance.*—None.

Stem description:

*Length.*—15 inches to 20 inches.

*Diameter.*—5 mm to 6 mm.

*Internode length.*—1 inch to 1.5 inches.

*Stem and internode coloration.*—RHS 144A.

*Strength.*—Medium.

*Branching.*—Freely.

*Pubescence.*—Present.

Foliage:

*Overall shape of leaf.*—Elliptic.

*Arrangement.*—Alternate.

*Apex.*—Obtuse.

*Base.*—Acute.

*Length.*—7.5 cm.

*Width.*—1 inch to 1.25 inches.

*Margin.*—Entire.

*Texture.*—Lustrous.

*Color of upper surface.*—Mature leaf: Yellow-Green RHS 147 A. Immature leaf: Yellow-Green RHS 146 A.

*Color of lower surface.*—Mature leaf: Yellow-Green RHS 146 A. Immature leaf: Yellow-Green RHS 146 A.

*Venation color.*—Upper surface: Yellow-Green RHS 144C. Lower surface: Yellow-Green RHS 144C.

*Petiole.*—Length: 1 inch.

*Diameter.*—4 mm.

*Color.*—Yellow-Green RHS 144C.

Inflorescence:

*Flower longevity.*—2 to 4 days.

*Flower size.*—Depth: 2 cm to 2.5 cm. Diameter: 4 cm to 5 cm.

*Flower shape.*—Trumpet.

*Average number of flowers per lateral branch.*—6 to 8.

*Floral tube.*—Diameter: 0.7 cm to 1.0 cm.

*Petals.*—Number: 5. Shape: Corolla united with 5 lobes and a long straight tube. Size: 2 inches in width; 4 to 5 cm in length from edge to the base of the floral tube. Apex: Truncate. Margin: Entire. Texture: Glabrous. Color: Upper surface: Red-Purple RHS 74A; and white RHS 155A. Lower surface: Red-Purple RHS 72C; and white RHS 155A.

*Sepals.*—Number: 5. Shape: Elliptic. Length: 25 mm. Width: 8 mm. Apex: Truncate. Margin: Entire. Texture: Lustrous. Color: Upper surface: Green RHS 137 A. Lower surface: Green RHS 137 B.

*Bud.*—Rate of opening: 7–10 days. Color: Apex of bud: Red-Purple RHS 72C; Base of bud: Green RHS 142 B. Shape: Flanged, composed of 5 petals ruled one around the other creating a cylindrical 5 winged shape. Length: 3.5 cm to 4 cm. Width: 0.5 cm. Diameter: 10 mm. Peduncle: 40 mm in length; green in color RHS 137 B.

Reproductive organs:

*Stamen.*—5 in number, white RHS 155 A.

*Anthers.*—White RHS 155 A.

*Filament.*—Yellow-Green RHS 145 B.

*Stigma.*—Yellow-Green RHS 146 C.

*Ovary.*—Yellow-Green RHS 146 C.

*Pollen.*—White RHS 155 A.

*Seed.*—Number: 40 to 50. Width: 1 mm. Length: 1 mm. Shape: Ovoid. Color: Brown RHS 200 C.

*Fruit.*—Number: Few, when naturally pollinated. Width: 4 mm. Length: 8 mm. Shape: Ellipsoid. Color: Gray-brown RHS 199 A.

Disease/pest resistance/susceptibility: Unknown.

I claim:

1. A new and distinct *Petunia* plant named 'Dancasbipas', as illustrated and described herein.

* * * * *

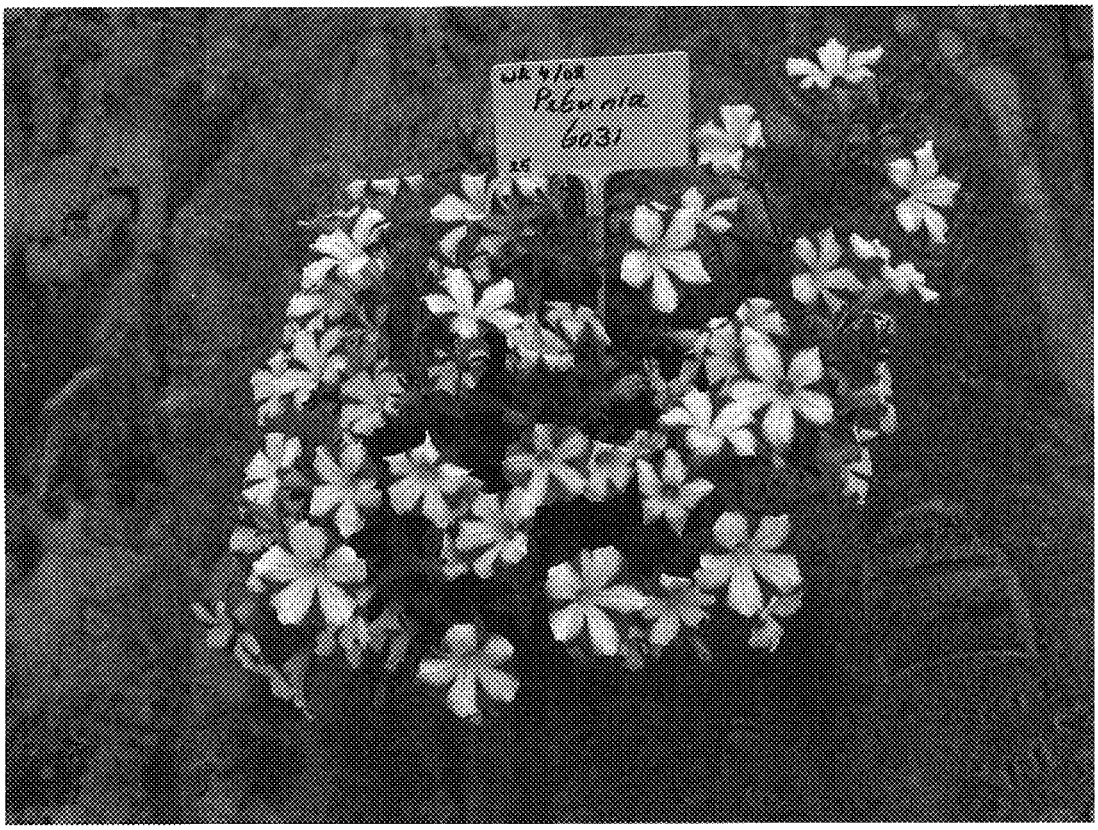

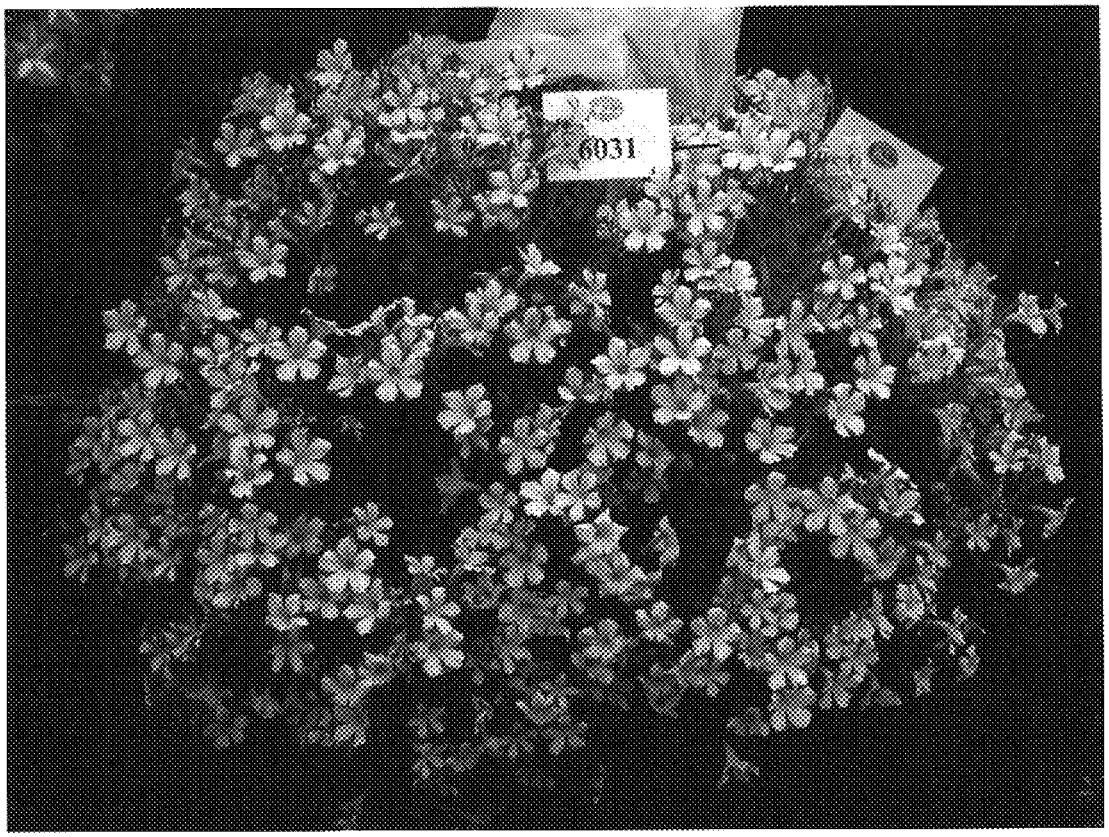
6031